United States Patent
Boin et al.

(10) Patent No.: US 10,391,527 B2
(45) Date of Patent: Aug. 27, 2019

(54) OZONE CLEANING SYSTEM AND METHOD OF OPERATING SAME

(71) Applicant: MAGNA CLOSURES INC., Newmarket (CA)

(72) Inventors: Luciano Boin, Richmond Hill (CA); Samuel Baruco, Aurora (CA); J. R. Scott Mitchell, Newmarket (CA)

(73) Assignee: MAGNA CLOSURES INC., Newmarket (CA)

( * ) Notice: Subject to any disclaimer, the term of this patent is extended or adjusted under 35 U.S.C. 154(b) by 0 days.

(21) Appl. No.: 15/113,237

(22) PCT Filed: Feb. 10, 2015

(86) PCT No.: PCT/CA2015/000072
§ 371 (c)(1),
(2) Date: Jul. 21, 2016

(87) PCT Pub. No.: WO2015/117233
PCT Pub. Date: Aug. 13, 2015

(65) Prior Publication Data
US 2017/0021397 A1    Jan. 26, 2017

Related U.S. Application Data

(60) Provisional application No. 61/937,948, filed on Feb. 10, 2014, provisional application No. 62/076,052, filed on Nov. 6, 2014.

(51) Int. Cl.
*B08B 5/00* (2006.01)
*C01B 13/11* (2006.01)
(Continued)

(52) U.S. Cl.
CPC .............. *B08B 5/00* (2013.01); *A61L 2/202* (2013.01); *C01B 13/10* (2013.01); *C01B 13/11* (2013.01);
(Continued)

(58) Field of Classification Search
CPC ......... C01B 13/11; C01B 13/10; A61L 2/202; A61L 2/28; A61L 2202/11; B08B 5/00; G01N 33/0039; D06L 4/50
See application file for complete search history.

(56) References Cited

U.S. PATENT DOCUMENTS 2,325,225 A * 7/1943 Burke ................. E05B 47/0002
292/123
2,849,250 A * 8/1958 Williamson ........ E05B 65/0053
109/63.5
(Continued)

FOREIGN PATENT DOCUMENTS

CA    2385170 A1    12/2002
CA    2508909 C     7/2004
(Continued)

OTHER PUBLICATIONS

NPL: Ozone Solutions, Ozone Compatible Materials Chart, Apr. 14, 2018.*
(Continued)

*Primary Examiner* — Benjamin L Osterhout
(74) *Attorney, Agent, or Firm* — Dickinson Wright PLLC

(57) ABSTRACT

An ozone cleaning system includes a cabinet defining a cleaning space, and an ozone generator disposed in fluid communication with the cleaning space and configured to produce and introduce ozone therein for cleaning items with ozone. An ozone neutralization unit is attached to the cabinet and includes an inlet and outlet tube each disposed within the cabinet. The ozone neutralization unit includes a heater/
(Continued)

blower assembly in fluid communication with each tube and operable for heating and recirculating the ozone within the cleaning space. A method of operating the ozone cleaning system includes receiving an input to commence an ozone cleaning cycle, and then producing and introducing ozone into the cleaning space. The method proceeds by determining if the ozone cleaning cycle is complete, and then initiating and executing an ozone neutralization cycle to accelerate the rate of ozone neutralization after the ozone cleaning cycle is complete.

19 Claims, 6 Drawing Sheets

(51) Int. Cl.
| | |
|---|---|
| *G01N 33/00* | (2006.01) |
| *A61L 2/20* | (2006.01) |
| *C01B 13/10* | (2006.01) |
| *D06L 4/50* | (2017.01) |
| *A61L 2/28* | (2006.01) |

(52) U.S. Cl.
CPC ............ *D06L 4/50* (2017.01); *G01N 33/0039* (2013.01); *A61L 2/28* (2013.01); *A61L 2202/11* (2013.01)

(56) References Cited

U.S. PATENT DOCUMENTS

| | | | | |
|---|---|---|---|---|
| 3,076,328 | A * | 2/1963 | Rhodes | E05B 63/0069 109/63.5 |
| 4,046,412 | A * | 9/1977 | Lee | E05B 5/00 292/200 |
| 4,625,432 | A * | 12/1986 | Baltes | A61L 2/06 34/196 |
| 5,266,275 | A * | 11/1993 | Faddis | A61L 2/202 422/116 |
| 5,445,326 | A | 8/1995 | Ferro et al. | |
| 6,433,292 | B1 | 8/2002 | Tate | |
| 8,006,336 | B1 * | 8/2011 | Gerlach | B05B 5/03 68/5 C |
| 2002/0051739 | A1 * | 5/2002 | Wang | A61L 2/202 422/105 |
| 2003/0126691 | A1 * | 7/2003 | Gerlach | D06F 35/001 8/158 |
| 2003/0143108 | A1 | 7/2003 | Wasinger | |
| 2004/0003511 | A1 * | 1/2004 | Silver | F26B 9/06 34/201 |
| 2005/0193585 | A1 * | 9/2005 | Silver | F26B 9/06 34/201 |
| 2007/0068552 | A1 * | 3/2007 | Willing | B08B 3/04 134/10 |
| 2007/0166186 | A1 * | 7/2007 | Stec | A01M 31/00 422/5 |
| 2008/0159910 | A1 * | 7/2008 | Dick | A23B 7/152 422/40 |
| 2010/0040515 | A1 * | 2/2010 | Lovelace | A61L 2/202 422/186.08 |
| 2011/0168517 | A1 * | 7/2011 | Krieger | E05C 3/14 192/135 |
| 2013/0199581 | A1 * | 8/2013 | Christopherson | B08B 5/026 134/103.2 |
| 2013/0224085 | A1 * | 8/2013 | Antinozzi | A61L 2/18 422/186.08 |
| 2014/0105783 | A1 * | 4/2014 | Levsen | A61L 2/202 422/5 |
| 2014/0193294 | A1 * | 7/2014 | Kain | A61L 2/24 422/3 |
| 2014/0205504 | A1 * | 7/2014 | Khoshbin | C01B 13/10 422/108 |
| 2017/0320734 | A1 * | 11/2017 | Pattee | C01B 13/10 |

FOREIGN PATENT DOCUMENTS

| | | | | |
|---|---|---|---|---|
| CA | 2526367 | A1 | 4/2007 | |
| CN | 201618175 | U | 11/2010 | |
| CN | 103480016 | A | 1/2014 | |
| EP | 2273004 | A1 * | 1/2011 | D06F 43/06 |

OTHER PUBLICATIONS

International Search Report and Written Opinion dated May 4, 2015 in corresponding International Patent Application No. PCT/CA2015/000072.

Search Report dated Sep. 11, 2018 from corresponding Chinese Patent Application No. 201580008072.3.

* cited by examiner

OZONE CLEANING SYSTEM AND METHOD OF OPERATING SAME

CROSS-REFERENCE TO RELATED APPLICATIONS

This application claims priority to and the benefit of U.S. Provisional Application No. 61/937,948, filed Feb. 10, 2014, and U.S. Provisional Application No. 62/076,052, filed Feb. 10, 2014, the entire disclosures of which are incorporated herein by reference.

FIELD

The present disclosure relates generally to an ozone cleaning system for reducing and removing bacteria from a variety of items. The present disclosure also relates to a method of operating an ozone cleaning system.

BACKGROUND

This section provides a general summary of background information and the comments and examples provided in this section are not necessarily prior art to the present disclosure.

Sports equipment, such as hockey and football equipment, readily develops odors, mold, and mildew after repeated use which can be often difficult to clean and dry using residential washers and dryers. Correspondingly, there has been a growing concern with the ability to adequately clean sports equipment as the spread of bacteria from the sports equipment to a user can often lead to serious health issues. As such, various commercial ozone cleaning systems have been specifically developed to clean sports equipment with ozone. In addition, other commercial ozone cleaning systems have been developed to clean bacteria from large spaces within a building as well as from other personal items such as clothing.

While commercial ozone cleaning systems of the type noted above operate satisfactorily for their intended purpose, these ozone cleaning systems are extremely large and fairly expensive to purchase and repeatedly operate. As such, these ozone cleaning systems are only feasible for commercial retailers, and thus are not readily available to the public for their personal use. Even in the instance that an ozone cleaning system is available to the public, it still requires that consumers commute to a commercial retailer to treat and clean their sports equipment and other personal items with the retailer's ozone cleaning system for a costly one-time fee.

As such, a recognized need exists to make further improvements to ozone cleaning systems in an effort to reduce their size and affordability and thus provide more access for the average consumer to clean their personal items with an ozone cleaning system. To this end, a specific need exists to develop an ozone cleaning system that is sized to be easily and readily positioned within a home or a smaller commercial environment, such as a hospital, doctor office, or dentist office, and that also provides for more affordable and economical repeated use within these environments. Such an ozone cleaning system would be advantageous because it would increase the availability of cleaning other personal items besides sport equipment with ozone, such as household items, medical items, and dental items, and thus provides an average consumer with a more sanitary lifestyle.

SUMMARY

This section provides a general summary of the present disclosure and is not intended to be interpreted as a comprehensive and exhaustive disclosure of all contemplated aspects, advantages, features and configurations.

It is an aspect of the present disclosure to provide an ozone cleaning system operable for reducing and eliminating bacteria from a variety of items.

It is another aspect of the present disclosure to provide a method of operating such an ozone cleaning system.

It is another aspect of the present disclosure to equip the ozone cleaning system with an ozone neutralization unit having a heated recirculation circuit.

These and other aspects of the present disclosure are provided by an ozone cleaning system for cleaning a variety of items with ozone comprising: a cabinet having a plurality of panels each extending from a bottom portion to a top portion to collectively define a cleaning space of said cabinet; a lid pivotably attached along said top portion of said cabinet and movable from an open position to a closed position to enclose said cleaning space, said lid including a striker assembly disposed in interlocking relationship with a latch assembly of said cabinet in said closed position; an ozone generator disposed in communication with said cleaning space and configured to produce and introduce ozone therein when said lid is disposed in said closed position for cleaning items disposed within said cleaning space with ozone; and a manual emergency release plate disposed on an underside of said lid and interconnected to said latch assembly for allowing a user trapped inside said cleaning space to manually push up on said manual emergency release plate and escape from said cabinet.

In accordance with another aspect of the present disclosure, the ozone cleaning system includes a controller disposed in electrical communication with the at least one ozone cell that is configured to monitor a current of the at least one ozone cell and determine an optimum operating frequency of the ozone generator using the monitored current. An ozone sensor is disposed in electrical communication with the controller and is in electrical communication with the cleaning space to detect a concentration level of ozone with the cleaning space of the cabinet. A visual display is disposed in electrical communication with the controller and is configured to provide operational feedback of the ozone cleaning system to a user and allow the user to interact with the ozone cleaning system.

In accordance with another aspect of the present disclosure, the ozone cleaning system includes an ozone neutralization unit comprising an inlet tube disposed within the cleaning space and having inlet ports, and an outlet tube disposed within the cleaning space and having discharge ports. A heater/blower assembly is in fluid flow communication with the inlet and outlet tubes, wherein the heater/blower assembly is operable to draw ozone from the cleaning space through the inlet ports, heat the ozone, and return the heated ozone to the cleaning space through the discharge ports, thereby establishing a recirculatory heat transfer system for accelerating the rate of ozone neutralization.

DRAWINGS

The drawings described herein are for illustrative purposes only of selected embodiments and not all possible implementations, and are not intended to limit the scope of the present disclosure.

DETAILED DESCRIPTION

Example embodiments of an ozone cleaning system constructed in accordance with the present disclosure will now be more fully described. Each of these example embodiments are provided so that this disclosure is thorough and fully conveys the scope of the inventive concepts, features and advantages to those skilled in the art. To this end, numerous specific details are set forth such as examples of specific components, devices and mechanisms associated with the ozone cleaning system to provide a thorough understanding of each of the embodiments associated with the present disclosure. However, as will be apparent to those skilled in the art, not all specific details described herein need to be employed, the example embodiments may be embodied in many different forms, and thus should not be construed or interpreted to limit the scope of the disclosure.

Figure 1:
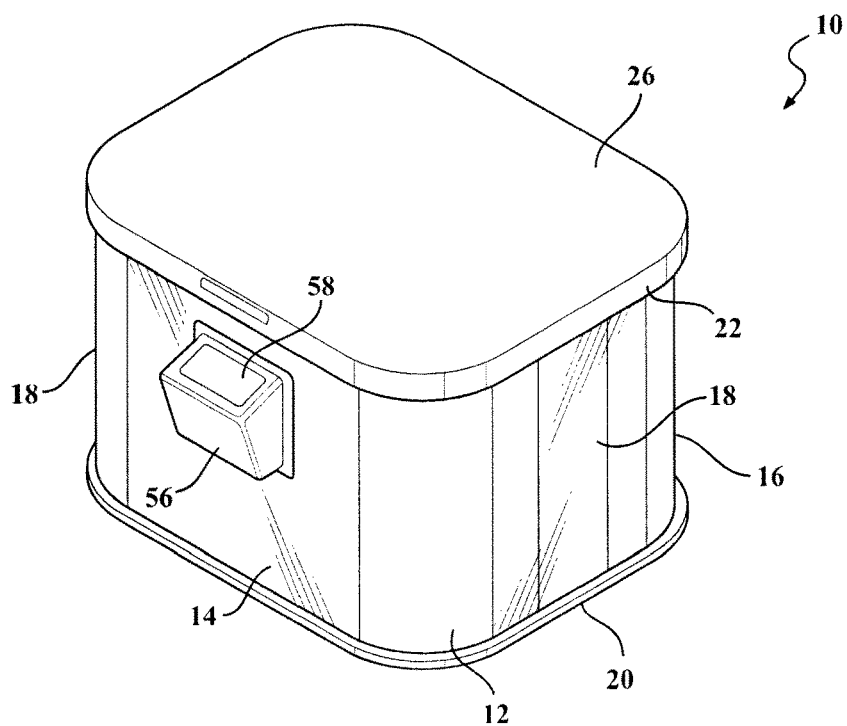
FIG. 1 is a perspective view of an ozone cleaning system constructed in accordance with the teachings of the present disclosure.
Figure 2:
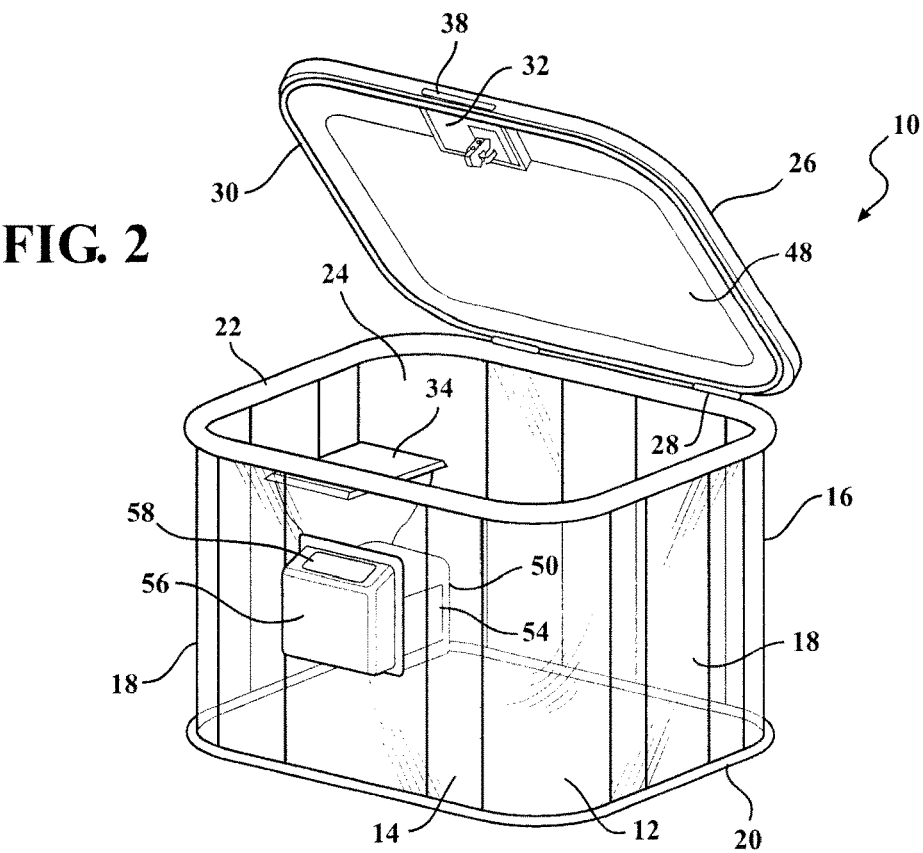
FIG. 2 is a perspective view of the ozone cleaning system with its lid disposed in an open position to illustrate a manual emergency release plate.

FIG. 1 is a perspective view of an ozone cleaning system 10 illustrating a cabinet 12 having a front panel 14, a rear panel 16, and a pair of side panels 18 each extending from a bottom portion 20 to an open top portion 22 of the cabinet 12. Although the ozone cleaning system 10 will be described hereinafter in conjunction with a cabinet 12, the features and method of the ozone cleaning system 10 described herein can also be incorporated into any other structure or a household appliance such as a washer, dryer, or dishwasher machine. As best shown in FIG. 2, each of the panels 14, 16, 18 collectively define an internal cleaning space 24 for receiving a variety of personal items to be cleaned and deodorized by ozone, such as medical devices, dental devices, cosmetic items, and various household items such as a tooth brush, a comb, toys, clothes, kitchen utensils, or any other personal items that can fit within the cleaning space 24. A lid 26 is pivotably connected to the cabinet 12 along the top portion 22 of the cabinet 12, and is movable from an open position, as shown in FIG. 2, to a closed position, as shown in FIG. 1. In an embodiment, the lid 26 is connected to the cabinet 12 using a hinge 28 which extends along the top portion 22 of the cabinet 12 adjacent the rear panel 16. However, any other means of connecting the lid 26 to the cabinet 12 could be utilized without departing from the scope of the subject disclosure. As also shown in FIG. 2, the lid 26 and/or the top portion 22 of the cabinet 12 can include sealing components such as, for example, silicone seals 30 or silicone caulking to hermetically seal the lid 26 with the cabinet 12 when the lid 26 is disposed in the closed position. This arrangement is advantageous because it takes up any manufacturing deficiencies that are present in the cabinet 12 or lid 26.

In one preferred embodiment, the cabinet 12 and the lid 26 are each constructed out of ozone resistive plastics, such as polycarbonate, high density polyethylene materials, or the like. The use of ozone resistive plastics is advantageous because it reduces the overall cost of the ozone cleaning system 10 while acting to isolate ozone disposed within the cleaning space 24 from being exposed to a user located externally to the ozone cleaning system 10. In addition, each of the panels 14, 16, 18, 20 or portions of any one of the panels 14, 16, 18, 20 can be constructed out of a transparent material to allow a visual confirmation and monitoring of the personal items disposed within the cleaning space 24 of the cabinet 12.

Figure 3:
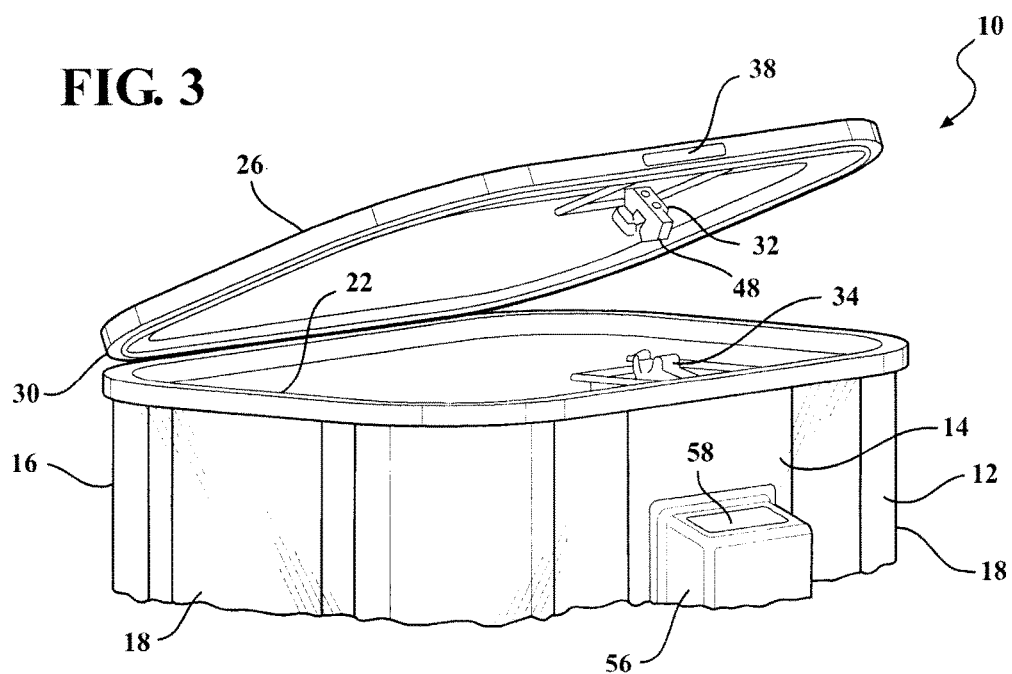
FIG. 3 is an exploded perspective view of the lid in the open position to more clearly illustrate the manual emergency release plate, as well as a striker assembly and a latch assembly of the ozone cleaning system.

As shown in FIGS. 2 and 3, the lid 26 includes a striker assembly 32 disposed on an underside of the lid 26 and the cabinet 12 includes a latch assembly 34 disposed on an inside of the front panel 14 and within the cleaning space 24. As mentioned previously, the lid 26 is pivotable between the open position and the closed position to permit access to and enclose the personal items within the cleaning space 24. When the lid 26 is disposed in the closed position, the striker assembly 32 is disposed in interlocking relationship with the latch assembly 34 to lock the lid 26 and prevent the lid 26 from opening without manual intervention. The lid 26 can also include a manual latch button 38 to allow a user to manually release the striker assembly 32 from the latch assembly 34. In a further embodiment, the striker assembly 32 and/or the latch assembly 34 could also include an electronic lock to prevent the opening of the cabinet 12, even in the presence of a manual intervention, once an ozone cleaning cycle of the ozone cleaning system 10 has begun. The electronic lock is advantageous because it can prevent the exposure of an operator/user to unsafe ozone levels, and can also be a pre-requisite to any ozone cleaning cycle, i.e. the ozone cleaning cycle will not begin until the electronic lock is activated. In an embodiment, the ozone cleaning system 10 can also include a limit switch built into either the striker assembly 32 or latch assembly 34 to provide a signal which indicates that the lid 26 is closed and the ozone cleaning cycle can commence. As will be described in more detail below, an ozone cleaning cycle of the ozone cleaning system 10 cannot commence until the lid 26 is locked and the lid 26 will be prevented from opening until an entire cleaning cycle has completed. In an additional embodiment, the ozone cleaning system 10 could also include a pop-up feature to indicate that the lid 26 is in the open position.

Figure 4:
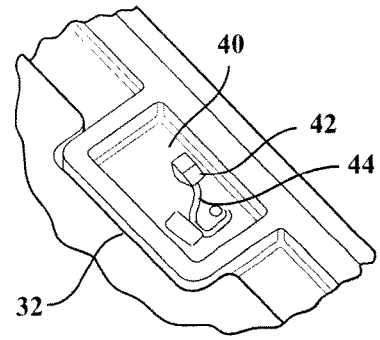
FIG. 4 is a magnified perspective view of a portion of FIG. 3. more clearly illustrating the components of the striker assembly.
Figure 5:
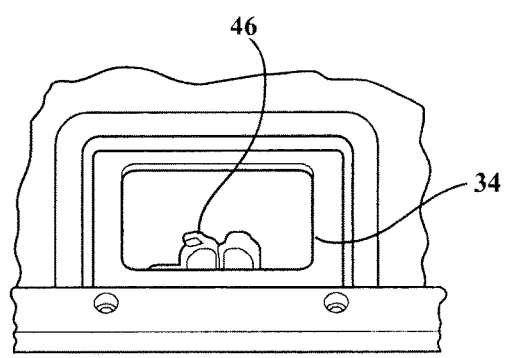
FIG. 5 is magnified perspective view of a portion of FIG. 3 more clearly illustrating the latch assembly.

As shown in FIG. 4, the striker assembly 32 includes an activation tab 40, a striker lever 42, and a cable 44. As shown in FIG. 5, the latch assembly 34 includes a latch lever 46. In an embodiment, the latch assembly 34 includes a power release latch. With further reference to FIGS. 2 and 3, the ozone cleaning system 10 can also include a manual emergency release plate 48 disposed on an underside of the lid 26. The manual emergency release plate 48 is interconnected to either the striker assembly 32 or the latch assembly 34 and designed to release the striker assembly 32 from the latch assembly 34, and override any electronic lock therebetween, in the event that someone is locked within the cleaning space 24 of the cabinet 12. In an embodiment, the manual emergency release plate 48 could be interconnected to an assembly similar to the "Over Travel Hood Latch" of U.S. patent application Ser. No. 13/981,201, the disclosure of which is incorporated herein by reference. In an alternative embodiment, the manual emergency release plate could be interconnected to a power lock/unlock latch capable of overriding the electronic lock. Such a power lock/unlock latch could be used if the ozone cleaning system 10 did not include a manual release button 38 disposed on an outside of the cabinet 12, or the manual release button 38 was designed such that it was not capable of overriding the electronic lock. One such example of a power lock/unlock latch is disclosed in U.S. Provisional Patent Application 61/930,699, entitled a "Door Latch Assembly For Motor Vehicles", the disclosure of which is incorporated herein by reference.

The manual emergency release plate 48 operates such that if someone is trapped within the cleaning space 24, the trapped occupant can simply push up on the manual emergency release plate 48, and the manual emergency release plate 48 will automatically release the latch assembly 34 from the striker assembly 32 to allow the trapped occupant to escape. For example, when a trapped occupant pushes up on the manual emergency release plate 48, the manual emergency release plate 48 will pull the cable 44 which is attached to the striker lever 42, causing the striker lever 42 to rotate. The activation tab 40, which is attached to the striker lever 42, also follows this rotation of the striker lever 42. The activation tab 40 will then push on the latch lever 46 of the latch assembly 34 to release the striker assembly 32 therefrom. Since the cleaning space 24 of the cabinet 12 is likely dark when the lid 26 is disposed in the closed and locked position, the manual emergency release plate 48 is designed to cover approximately 90% of the underside of the lid 26 such that if an occupant was locked inside, all they would need to do is push up on the lid 26 to release the lock.

Figure 6:
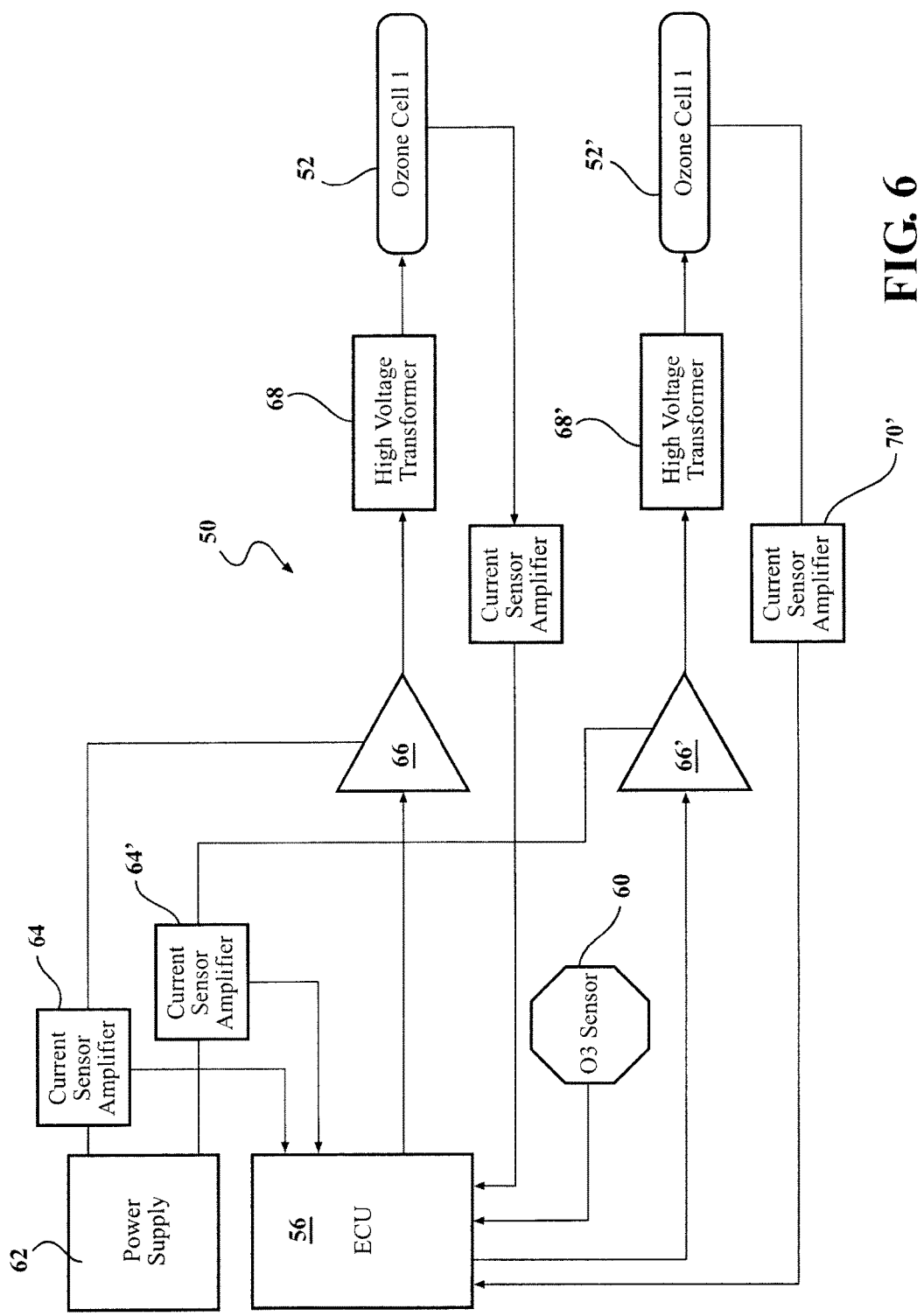
FIG. 6 is a block diagram of an ozone generator constructed in accordance with a preferred embodiment of the ozone cleaning system.

As best shown in FIG. 2, the ozone cleaning system 10 includes an ozone generator 50 disposed in communication with the cleaning space 24 of the cabinet 12, and in the preferred embodiment, is attached to the inside of the front wall 14 of the cabinet 12. However, the ozone generator 50 could also be attached to any of the walls 14, 16, 18 without departing from the scope of the subject disclosure. As best shown in FIG. 6, the ozone generator 50 includes at least one ozone cell 52, such as corona discharge cell or an ultra-violet cell, with the number of ozone cells 52 depending on the ozone concentration levels that are required within the cleaning space 24. In the preferred embodiment, the ozone cell(s) 52 are designed to produce at least ozone concentration levels up to 100 ppm, with a target of 50 ppm, within the cleaning space 24. As best shown in FIG. 2, the ozone generator includes a vent 54 disposed in communication with the ozone cell(s) 52 to allow the ozone produced by the ozone cell(s) 52 to pass into the cleaning space 24. In addition, a fan (not expressly shown) is disposed between the ozone cell(s) 52 and the vent 54 to circulate the ozone within the cleaning space 42 as well as cool the ozone cell(s) 52.

As best shown in FIGS. 1 and 2, the ozone cleaning system 10 also includes a controller 56 that is disposed on an outside surface of the cabinet 12 and in electrical communication with the ozone generator 50. If the ozone generator 50 is disposed on an inside of the front wall 14, as shown in FIG. 2, the controller 56 is preferably disposed next adjacent the ozone generator 50 on an outside of the front panel 14. The mounting of the controller 56 on an outside of the cabinet 12 is advantageous because it isolates, and thus protects, the controller 56 and its associated electronics from the ozone introduced into the cleaning space 24 by the ozone generator 50. In an embodiment, the electronic locking mechanism and the fan motor can also be isolated, and thus protected, from the ozone produced within the cleaning space 24.

As best shown in FIGS. 1 and 3, the ozone cleaning system 10 includes a visual display 58 in electrical communication with the controller 56 to provide operational feedback to a user and allow the user to interact with the ozone cleaning system 10. For example, the visual display 58 could provide lighting to indicate a start of an ozone cleaning cycle, provide an indication of a time remaining in the ozone cleaning cycle, provide an indication of an ozone concentration during the ozone cleaning cycle, as well as providing an indication of an end of the ozone cleaning cycle. As such, the visual display 58 can be used to provide an indication to an operator of the status of the ozone cleaning cycle. In an embodiment, the visual display 58 could also include a touch screen display to allow an operator to initiate an ozone cleaning cycle of the ozone cleaning system 10.

As shown in FIG. 6, the ozone cleaning system 10 can also include an ozone sensor 60 disposed in electrical communication with the controller 56 and in communication with the cleaning space 24 to detect an amount or concentration level of ozone within the cleaning space 24. This feedback from the ozone sensor 60 could then be used by the controller 56 to regulate the amount of ozone production by the ozone generator 50. For example, the ozone sensor 60 could be utilized to automatically increase or decrease ozone production by the ozone generator 50 for purposes of maintaining a specific ozone concentration within the cleaning space 24. One suitable ozone sensor could be a MQ131 ozone sensor from Winsen Sensor, however other ozone sensors could be used without departing from the scope of the disclosure. In addition, the ozone sensor 60 could be used to determine when the electronic lock could be released to allow the lid 26 of the ozone cleaning system 10 to be opened. For example, the ozone sensor 60 could be used to detect when an ozone concentration level of 0 ppm is present in the cleaning space 24 after completion of the ozone cleaning cycle, and used to keep the lid 26 locked until the ozone is no longer present in the cleaning space 24. Accordingly, the electronically controlled locking function, as regulated by the ozone sensor 60, ensures that any ozone which remains in the cleaning space 24 has been reverted back to oxygen before the lid 26 can be opened by the operator.

FIG. 6 is an example of a block diagram of the ozone generator 50 of the subject disclosure which incorporates two ozone cells 52, 52'. However, as previously mentioned above, the subject ozone cleaning system could also include only a single ozone cell, in which the duplicate parts for the second ozone cell would be omitted from the subject ozone generator block diagram. However, as shown in FIG. 6, in the event that two ozone cells 52, 52' are utilized, each of the ozone cells 52, 52' can be controlled independently. In view of the similarity between the control circuit for each of the ozone cells 52, 52', prime numbers are used in the drawings to identify the components of the second ozone cell 52' that are common with or similar to the components of first ozone cell 52 described hereafter.

With further reference to FIG. 6, the ozone generator 50 includes a power supply 62 electrically connected to a first current sensor amplifier 64. In an embodiment, the power supply 62 is a 12V power supply and the first current sensor amplifier 64 monitors current to ensure components within the ozone generator 50 do not draw too much current for preventing damage to the power supply 60. As shown in FIG. 6, the first current sensor amplifier 62 is electrically connected to a first High Voltage (HV) amplifier 66 which is electrically connected to a first High Voltage (HV) transformer 68. In an embodiment, the first HV amplifier 66 applies voltage for FET's, and the first HV transformer 68 steps up the voltage for the ozone generator 50 from 12 Volts to 6,000 Volts. The first HV transformer 68 is electrically connected to the first ozone cell 52 which is used to create ozone within the cleaning space 24, preferably through a corona discharge effect. The first ozone cell 52 is then electrically connected to a second current sensor amplifier 70 which measures, current being used by the ozone cell 52. The second current sensor amplifier 70 is electrically connected to the controller 56 and feeds the current being used by the first ozone cell 52 to a 10-bit analog to digital converter disposed within the controller 56.

As further shown in FIG. 6, the controller 56 is electrically connected to the first HV amplifier 66 and has a pulse width modulating (PWM) hardware module to control the operating frequency of the ozone generator 50. As will be described in more detail below, the controller 56 monitors the current of the first ozone cell 52 to determine/search for the optimum operating frequency of the ozone generator 50. As will be understood from the entirety of the subject disclosure, the controller 56 also controls the ozone cleaning and neutralization cycles, controls the electronic lock operation, senses ozone concentration levels within the cleaning space 24, auto-tunes the ozone cells 52, 52', and detects the lid 26 position. Although not expressly shown, a supercapacitor could be used in the circuitry of the ozone generator block diagram to provide temporary memory retention in the event of a power failure for the ozone generator 50.

Figure 7:
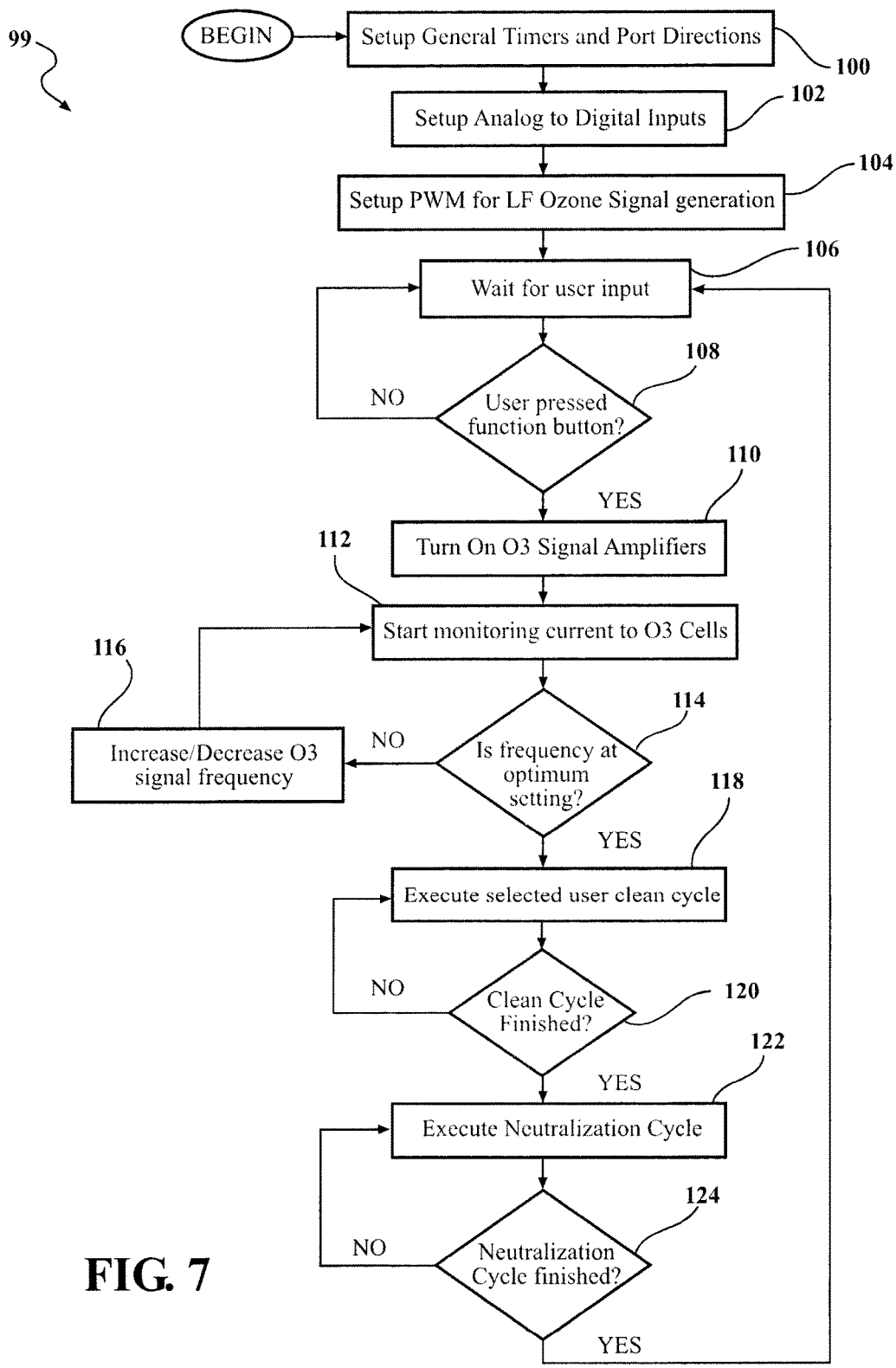
FIG. 7 is a flow diagram illustrating a method of operating the ozone cleaning system.

FIG. 7 is a flow chart illustrating the various steps or operations associated with an example method 99 for operating the ozone cleaning system 10. As shown in FIG. 7, the method 99 includes the steps or operations illustrated by block 100 for setting up general times and port directions, block 102 for setting up analog to digital inputs, and block 104 for setting up pulse width modulation (PWM) for LF zone signal generation. In a preferred embodiment, each of these steps would occur prior to delivery of the ozone cleaning system 10 to a consumer. Once the ozone cleaning system 10 is installed within a home, doctor's office, dentist's office, or the like, the method 99 proceeds to block 106 indicating the step of waiting for a user input at the ozone cleaning system 10, such as the pressing of a capacitive sensing button or the pressing of a visual indicator on the visual display 58. Once the ozone cleaning system determines, as shown by determination block 108, that the user has pressed a function button, the method 99 proceeds to block 110 whereat the controller 56 turns on the ozone signal amplifier(s) 70, and then to block 112 whereat the controller 56 monitor a current being delivered to the ozone cell(s) 52. As noted in FIG. 6, the optimum operating current is determined by the ozone cell(s) 52 and the on board power supply.

Since the ozone cells 52, 52' may have different characteristic impedances, the subject method includes method steps to match the specific characteristic impedances of the ozone cells 52, 52' to the respective high voltage amplifier 66, 66'. Put another way, the subject method includes steps to electronically self-adjust the ozone optimization process. Accordingly, the subject method proceeds to determination block 114 whereat the controller 56 determines if the frequency is at an optimum setting, and if it is not, proceed to block 116 whereat the controller 56 increases or decreases the ozone signal frequency as required.

The method determines the optimum operating frequency by monitoring the current, keeping in mind that the operational current has to be kept below the power supply maximum output current. In more detail, since the ozone cell impedance tolerance varies by up to 10%, the controller 56 gradually ramps up the frequency from approximately 14 kHz to 16 kHz. While this is happening, the analog to digital converter monitors the current. At the resonant frequency the current dips, and thus this is the dip that the controller 56 is monitoring. The controller 56 records this dip and sets the operational frequency of the ozone cell 52 to the now known resonant frequency.

Once this optimum frequency setting has been established by the controller 56, the method proceeds to block 118 whereat the user selected clean cycle is executed to begin producing ozone within the cleaning space 24 using the ozone generator 50. In an example embodiment, the user could select either a "surface clean" cycle or a "deep clean" cycle by way of the visual display 58, with each of these cycles varying based on cycle time and/or targeted ozone concentration within the cleaning space 24. As the ozone is produced and introduced into the cleaning space 24, the ozone acts to break down various forms of bacteria that may be present on the personal items disposed within the cabinet 12. Once selected, the method proceeds to determination block 120 whereat the controller 120 determines if the selected ozone cleaning cycle is finished, for example by determining if the required time has elapsed for the selected ozone cleaning cycle.

If the clean cycle is complete, the controller 56 proceeds, as shown by block 122, to initiate and execute a neutralization cycle for allowing the ozone present within the cabinet 12 to revert back to oxygen. In one embodiment of the ozone cleaning system 10, the neutralization cycle may simply consists of allowing the cabinet 12 to remain closed and latched for a predetermined period of time to allow all of the ozone to revert back to oxygen naturally. In addition, and as mentioned above, the neutralization cycle could also continue until the ozone sensor 60 senses 0 ppm of ozone within the cabinet 12.

Method 99 subsequently moves to determination block 124 whereat controller 56 determines whether or not the ozone neutralization process has finished. Once the neutralization cycle is finished, for example by determining if the required time has elapsed or the ozone sensor 60 indicates 0 ppm of ozone within cabinet 12, the lid 26 may be released and opened to permit removal of the sanitized and cleaned items.

In another embodiment of the ozone cleaning system 10, a catalyst could also be introduced into the cleaning space 24 to neutralize the ozone and speed up the neutralization cycle. In any event, once the neutralization cycle is complete, the user is only then able to unlock the lid 26 and remove the personal items from the cabinet 12. The ozone cleaning system 10 then proceeds to await another user input from the user to commence a subsequent cleaning cycle.

Figure 8:
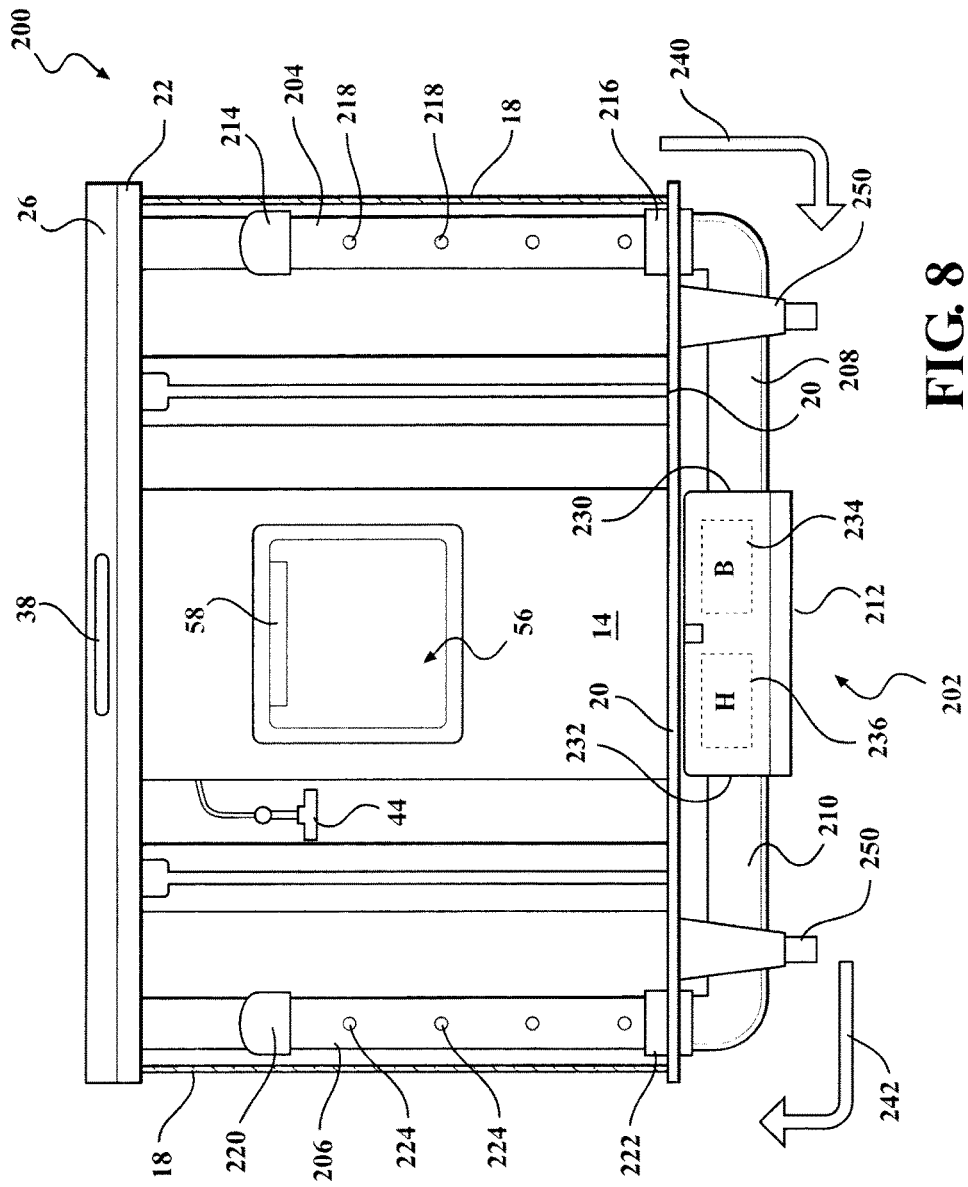
FIG. 8 is a front view of an ozone cleaning system constructed in accordance with an alternative embodiment of the present disclosure and which incorporates an ozone neutralization unit having a heated recirculation circuit.

Referring now to FIG. 8, an alternative embodiment of an ozone cleaning system 200 is shown. In general, ozone cleaning system 200 is substantially similar in structure and function to ozone cleaning system 10 with the exception that a neutralizer unit 202 has been integrated for the purpose of accelerating the neutralization cycle and reducing the time required to revert the ozone back to oxygen. Based on the similarity of most components, the components of ozone cleaning system 200 that are similar to those of ozone cleaning system 10 will be identified by common reference numerals.

Neutralizer unit 202 includes an inlet tube 204, an outlet tube 206, an inlet coupler tube 208, an outlet coupler tube 210, and a heater/blower assembly 212. Inlet tube 204 is disposed within cleaning space 24 against an inner surface of one of side panels 18 in a generally vertical orientation. Inlet tube 204 has an upper end closed by an inlet cap 214, a lower end installed within an inlet joint tube 216, and a plurality of inlet ports 218. Inlet joint tube 216 has a first end which extends through and is sealed relative to bottom panel 20 of cabinet 12 and which is configured to accept and retain the lower end of inlet tube 204 therein. As seen, a second end of inlet joint tube 216 extends outwardly from bottom panel 20 to be located external to cleaning space 24. Similarly, outlet tube 206 is disposed within cleaning space 24 against an inner surface of the other one of side panels 18 in a generally vertical orientation. Outlet tube 206 has an upper end closed by an outlet cap 220, a lower end installed within an outlet joint tube 222, and a plurality of discharge ports 224. Outlet joint tube 222 has a first end which extends through and is sealed relative to bottom panel 20 of cabinet 12 and which is configured to accept and retain the lower end of outlet tube 206 therein. A second end of outlet joint tube 222 extends outwardly from bottom panel 20 to be located external to cleaning space 24.

Heater/blower assembly 212 is shown to be installed below bottom panel 20 of cabinet 12 and define an inlet 230 and an outlet 232. Inlet coupler tube 208 is interconnected between the second end of inlet joint tube 216 and inlet 230 of heater/blower assembly 212. Likewise, outlet coupler tube 210 is interconnected between the second end of outlet joint tube 222 and outlet 232 of heater/blower assembly 212. Heater/blower assembly 212 is schematically shown to include a blower unit (B) 234 and a heater unit (H) 236. Ozone within internal chamber 24 is drawn into heater/blower assembly 212 upon actuation of blower unit 234 via an inlet flow path comprised of inlet ports 218, inlet tube 204, inlet joint tube 216, and inlet coupler tube 208. While not limited thereto, blower unit 234 may include an electric motor and fan assembly that is controlled by controller 56. It is contemplated that the flow characteristic of blower unit 234 can be variably controlled during the ozone neutralization process.

The ozone drawn into heater/blower assembly 212 by blower unit 234 subsequently flows through heater unit 236 where its temperature is increased to accelerate the ozone neutralization process. While not limited thereto, heater unit 236 may include an electric heater coil that is controlled by controller 56. As such, heater unit 236 acts as a heat exchange device configured to transfer heat to the ozone flowing through heater/blower assembly 212. The heated ozone is discharged from outlet 232 of heater/blower assembly 212 and returned to chamber 24 via an outlet flow path comprised of outlet coupler tube 210, outlet joint tube 222, outlet tube 206 and discharge ports 224. It is contemplated that the temperature of the ozone/air mixture flowing through heater/blower assembly 212 will be capable of being increased from ambient to about 58° C. Furthermore, this recirculatory system not only accelerates ozone reversion based on the increased temperature, but also due to the increased flow characteristic within, around and through chamber 24. Arrow 240 indicates the inlet flow direction while arrow 242 indicates the outlet flow direction with respect to heater/blower assembly 212.

In accordance with example cycle times for the neutralization cycle, it is contemplated that heater/blower assembly 212 would run for about 22 minutes following completion of the ozone generation process for the "surface clean" cycle and for about 40 for the "deep clean" cycle.

Figure 9:
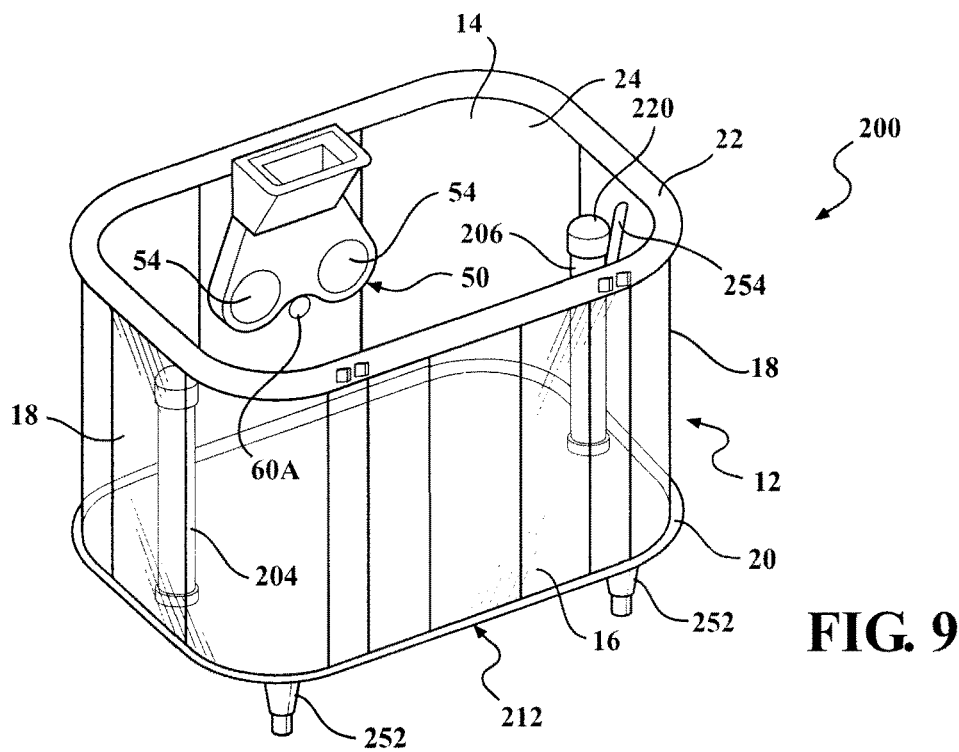
FIG. 9 is a perspective view of the ozone cleaning system of FIG. 8 with its lid removed for additional clarity to illustrate the location of an internal ozone sensor.
Figure 10:
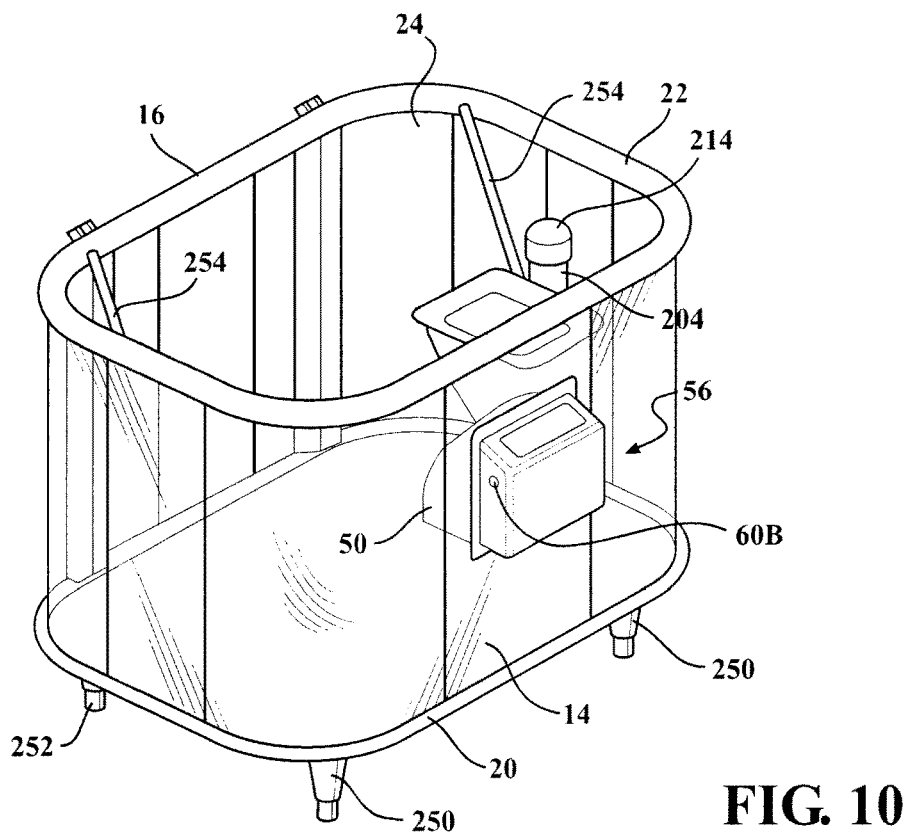
FIG. 10 is another perspective view of the ozone cleaning system shown in FIG. 8 with its lid removed for additional clarity to illustrate the location of an external ozone sensor.

FIGS. 9 and 10 illustrate ozone cleaning system 200 with lid 26 removed for additional clarity to show the location of an internal ozone sensor 60A and an external ozone sensor 60B. In particular, internal ozone sensor 60A is shown associated with ozone generator 50 while external ozone sensor 60B is shown associated with controller 56. To provided clearance for neutralizer unit 202, cabinet 12 is shown in FIGS. 8-10 to be mounted on front legs 250 and rear legs 252. Extension devices, such as struts 254 are also shown for interconnecting a portion of lid 26 to cabinet 12 to provide a counterbalance against the weight of lid 26.

Those skilled in the art will recognize that blower unit 234 of heater/blower assembly 212 associated with neutralizer unit 202 can include any suitable device capable of establishing an airflow circuit between inlet tube 204 and outlet tube 206. Likewise, this disclosure contemplates any suitable heat transfer device for use as heater unit 236 that is capable of transferring heat to the air/ozone flowing therethrough. While noted as being controlled by controller 56, a separate control unit can be used for heater/blower 212 assembly if so desired or applicable to another configuration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An ozone cleaning system for cleaning a variety of items with ozone comprising:
   a cabinet having a plurality of panels each extending from a bottom portion to a top portion to collectively define a cleaning space of said cabinet;
   a lid pivotably attached along said top portion of said cabinet and movable from an open position to a closed position to enclose said cleaning space, said lid including a striker assembly disposed in interlocking relationship with a latch assembly of said cabinet in said closed position;
   an ozone generator including a vent disposed in communication with said cleaning space and configured to produce and introduce ozone therein when said lid is disposed in said closed position for cleaning items disposed within said cleaning space with ozone; and
   an ozone neutralization unit attached to the cabinet and including an inlet tube disposed within said cleaning space of said cabinet, an outlet tube disposed within said cleaning space of said cabinet, and a blower assembly in fluid communication with said inlet and outlet tubes and operable for recirculating the ozone for accelerating the rate of ozone neutralization, wherein the inlet and outlet tubes include ports that are separate from the vent of the ozone generator;

a catalyst disposed in the cleaning space for accelerating the rate of ozone neutralization; and further comprising a manual emergency release plate moveably attached to said lid for allowing a user trapped inside said cleaning space to manually push up on said manual emergency release plate and escape from said cabinet, wherein the manual emergency release plate is interconnected to either the striker assembly or the latch assembly and designed to release the striker assembly from the latch assembly, and override any electronic lock therebetween.

2. The ozone cleaning system of claim 1 wherein said cabinet and said lid are comprised of ozone resistive plastics.

3. The ozone cleaning system of claim 1 further including a manual emergency release plate disposed on an underside of said lid and interconnected to said latch assembly for allowing a user trapped inside said cleaning space to manually engage said release plate and release said lid, wherein said manual emergency release plate is designed to cover about 90% of said underside of said lid.

4. The ozone cleaning system of claim 1 wherein said ozone generator includes at least one ozone cell.

5. The ozone cleaning system of claim 4 wherein said at least one ozone cell is a corona discharge cell.

6. The ozone cleaning system of claim 4 further comprising:
a controller disposed in electrical communication with said at least one ozone cell and configured to monitor a current of said at least one ozone cell and determine an optimum operating frequency of said ozone generator using said monitored current.

7. The ozone cleaning system of claim 6 further comprising:
an ozone sensor disposed in electrical communication with said controller and in electrical communication with said cleaning space to detect a concentration level of ozone within said cleaning space of said cabinet.

8. The ozone cleaning system of claim 6 further comprising:
a visual display disposed in electrical communication with said controller and configured to provide operational feedback of the ozone cleaning system to a user and allow the user to interact with the ozone cleaning system.

9. The ozone cleaning system of claim 1 wherein said inlet tube extends through said bottom portion of said cabinet and is aligned with one of the plurality of panels, said inlet tube having an inlet port communicating with said cleaning space, wherein said outlet tube extends through said bottom portion of said cabinet and is aligned with another one of the plurality of panels, said outlet tube having a discharge port communicating with said cleaning space, and wherein said heater/blower assembly is mounted to an underside of said bottom portion of said cabinet and has an inlet in fluid communication with said inlet tube and an outlet in fluid communication with said outlet tube.

10. The ozone cleaning system of claim 1, wherein the blower assembly comprises a heating unit for heating the ozone for accelerating the rate of ozone neutralization.

11. An ozone cleaning system for cleaning a variety of items with ozone comprising:

a cabinet having a plurality of panels each extending from a bottom portion to a top portion to collectively define a cleaning space of said cabinet;

a lid pivotably attached along said top portion of said cabinet and movable from an open position to a closed position to enclose said cleaning space;

said lid including a striker assembly disposed in interlocking relationship with a latch assembly of said cabinet in said closed position, the striker assembly and/or the latch assembly also including an electronic lock to prevent the opening of the cabinet;

an ozone generator disposed in communication with said cleaning space and configured to produce and introduce ozone therein when said lid is disposed in said closed position and the electronic lock is activated for cleaning items disposed within said cleaning space with ozone; and further comprising a manual emergency release plate moveably attached to said lid for allowing a user trapped inside said cleaning space to manually push up on said manual emergency release plate and escape from said cabinet, wherein the manual emergency release plate is interconnected to either the striker assembly or the latch assembly and designed to release the striker assembly from the latch assembly, and override any electronic lock therebetween.

12. The ozone cleaning system of claim 11 wherein said cabinet and said lid are comprised of ozone resistive plastics.

13. The ozone cleaning system of claim 11 wherein said manual emergency release plate is designed to cover about 90% of said underside of said lid.

14. The ozone cleaning system of claim 11 further comprising an ozone neutralization unit attached to the cabinet and including an inlet tube disposed within said cleaning space of said cabinet, an outlet tube disposed within said cleaning space of said cabinet, and a blower assembly in fluid communication with said inlet and outlet tubes and operable for recirculating the ozone for accelerating the rate of ozone neutralization; and a catalyst disposed in the cleaning space for accelerating the rate of ozone neutralization.

15. The ozone cleaning system of claim 11, wherein an ozone cleaning cycle will not begin until the electronic lock is activated.

16. The ozone cleaning system of claim 15, further comprising a limit switch built into either the striker assembly or the latch assembly to provide a signal which indicates that the lid is closed and the ozone cleaning cycle can commence.

17. The ozone cleaning system of claim 11, wherein the lid is prevented by the electronic lock from opening until an entire cleaning cycle has completed.

18. The ozone cleaning system of claim 11, further comprising a pop-up feature to indicate that the lid is open.

19. The ozone cleaning system of claim 11, wherein the system includes an internal and an external ozone sensor for detecting internal and external concentration levels of ozone, wherein the ozone sensor is used to determine when the electronic lock could be released to allow the lid of the ozone cleaning system to be opened.

* * * * *